(12) United States Patent
Rahman et al.

(10) Patent No.: US 11,103,529 B1
(45) Date of Patent: Aug. 31, 2021

(54) ZERO-VALENT GOLD NANOPARTICLES AS A CANCER THERAPY

(71) Applicant: King Abdulaziz University, Jeddah (SA)

(72) Inventors: Mohammed Muzibur Rahman, Jeddah (SA); Abdullah Mohamed Asiri, Jeddah (SA); Firoz A. D. M. Opo, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/141,589

(22) Filed: Jan. 5, 2021

(51) Int. Cl.
*A61K 33/242* (2019.01)
*A61P 35/00* (2006.01)
*A61K 9/51* (2006.01)

(52) U.S. Cl.
CPC .............. *A61K 33/242* (2019.01); *A61K 9/51* (2013.01); *A61P 35/00* (2018.01)

(58) Field of Classification Search
None
See application file for complete search history.

(56) References Cited

U.S. PATENT DOCUMENTS

| 9,669,103 | B2 * | 6/2017 | Lee ....................... A61K 31/713 |
| 2012/0277283 | A1 * | 11/2012 | Mirkin ................. A61K 31/713 |
| | | | 514/44 A |
| 2015/0150994 | A1 * | 6/2015 | Hahn ................. A61K 38/1833 |
| | | | 424/85.7 |

FOREIGN PATENT DOCUMENTS

WO    WO 2018/141940 A1 *    8/2018    ............... A61K 9/00

OTHER PUBLICATIONS

Taghizadeh et al., Photodiagnosis and Photodynamic Therapy (2019), vol. 25, pp. 389-400.*
Abdelhalim et al., Lipids in Health and Disease (2011), vol. 10:195, pp. 1/1-9/9.*
Xia Qiyue et al., Journal of Biomedical Materials Research, Part A (2017), 105(3), pp. 710-719.*

* cited by examiner

*Primary Examiner* — Brian J Davis
(74) *Attorney, Agent, or Firm* — W & C IP

(57) ABSTRACT

Provided herein are methods of killing cancer cells, comprising contacting the human liver cancer cells with a solution comprising zero-valent spherical $Au^\circ$ nanoparticles. Methods of treating liver cancer are also provided.

7 Claims, 10 Drawing Sheets

Control 0hr

Control 24hr

AuNPs 0hr

AuNPs 150ul

AuNPs 200ul

AuNPs 250ul

ZERO-VALENT GOLD NANOPARTICLES AS A CANCER THERAPY

FIELD OF THE INVENTION

The invention is generally related to zero-valent gold nanoparticles (Au° NPs) useful for the treatment of cancer and methods of synthesis thereof.

BACKGROUND OF THE INVENTION

Low-dimensional metallic nanoparticles have attracted huge attention in recent years due to their numerous applications in drug-delivery, biomedicine, electronics, electrocatalysis, and sensing as well as bio-sensing [1-6]. Target drug delivery is accomplished via the surface chemistry of the nanoparticles for the selective attachment drugs as well as targeting agents in biological systems. In chemotherapeutic treatments, the large surface area permits the drug molecule to carry a large payload of cancer drugs to the cancer affected sites [7]. The higher density of low-dimensional gold nanoparticles and their capacity to absorb X-rays makes them useful as a contrast agent for X-ray [8].

Surface Plasmon Resonance occurs when electrons in the conduction band of a nanomaterial stimulated by an incident light oscillate collectively at the interface between negative and positive permittivity materials [10]. Surface Plasmon Resonance makes the surface of low-dimensional gold nanoparticles very sensitive to external influence [11-14]. The shifting of the plasmon band is measured by UV-visible spectrometry due to the nanomaterial encountered on the surface of gold nanoparticles [15]. It occurs due to the change of refractive index of the transmitted medium [16, 17]. Changes in the wavelength occur due to the plasmon coupling between the closely packed gold nanoparticles, which are held when the nano-dimensional gold nanoparticles aggregate. This is the main cause of sensing or killing the cancer cell in a biological system [18,19].

The recent advancement of nanotechnology led to the production of various nano products to treat and diagnose cancer with a specific diameter of 40 to 400 nm [20,21]. Different materials are used to produce nano particles and quantum dots including liposomes, polymers, inorganic materials such as silver, gold, cadmium, zinc, etc. and proteins [22-24]. Among these different nano particles, Au nanoparticles are inert, are not easily oxidized in the presence of oxygen, and have different colors based on their size, shape and accumulation or aggregation properties [25,26]. Particle size is an important parameter which affects the surface of particles which exhibit different types of structures such as quantum, nano-, micro-, and macrostructures.

The most common malignant cancer is known as hepatic cancer. Early diagnosis is difficult and the common treatment methods such as surgery, chemotherapy and radiation therapy produce many side effects. Therefore, alternative treatments are gaining popularity [27]. Gold nanoparticles are widely used in anti-cancer therapy [31,32]. These particles work as a carrier to carry many water insoluble anticancer drugs such as camptothecin to the target area [33]. The endocytosis process delivers the nano-particles to the lysosome which are adjacent to the nucleus and inhibit the growth of cells [34]. Different sizes of gold nanoparticles have the ability to inhibit the progression as well as the anticancer activity of dendritic cells as the tissue environment has a significant role for advancement of tumor and metastasis [35,36].

New formulations comprising zero-valent gold nanoparticles (Au° NPs) for anti-cancer therapy are needed.

SUMMARY

Described herein are zero-valent gold nanoparticles (Au° NPs) having an increased therapeutic efficiency for destroying cancer cells via the apoptosis pathway and formation of reactive oxygen species.

An aspect of the disclosure provides a method of killing liver cancer cells, comprising contacting the cancer cells with a solution comprising zero-valent spherical gold nanoparticles. In some embodiments, the liver cancer cells are hepatic cancer cells. In some embodiments, the zero-valent gold nanoparticles have a size of 10-20 nm. In some embodiments, the zero-valent gold nanoparticles (Au° NPs) are present in the solution at a concentration of at least 40.0 µM. In some embodiments, the zero-valent nanoparticles are not coated with any other molecule. In some embodiments, the cancer cells are not contacted with any other anti-cancer agent. In some embodiments, the zero-valent nanoparticles (Au° NPs) produce reactive oxygen species (ROS) and/or induce apoptosis of the cancer cells.

Another aspect of the disclosure provides a method of treating cancer in a subject in need thereof, comprising administering to the subject a therapeutically effective amount of a composition comprising zero-valent spherical gold nanoparticles (Au° NPs). In some embodiments, the subject suffers from hepatic cancer. In some embodiments, the zero-valent gold nanoparticles (Au° NPs) have a size of 10-20 nm. In some embodiments, the zero-valent gold nanoparticles (Au° NPs) are present in the composition at a concentration of at least 40.0 µM. In some embodiments, the spherical zero-valent gold nanoparticles (Au° NPs) are not coated with any other molecule. In some embodiments, the zero-valent gold nanoparticles are administered without any other anti-cancer agent. In some embodiments, the zero-valent gold nanoparticles (Au° NPs) are administered in an amount sufficient to produce reactive oxygen species (ROS) and/or induce apoptosis of cancer cells.

(B) Inhibition of cell death increased with the increasing volume of zero-valent gold nanoparticles (Au° NPs).

Figure 6:
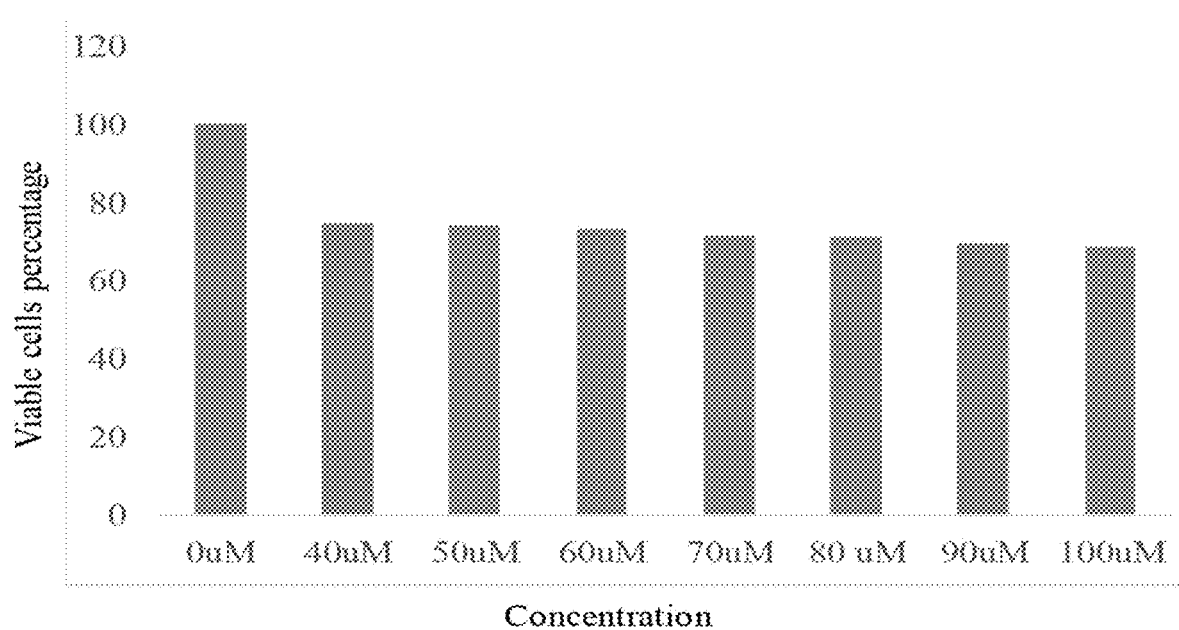

FIG. 6. Hep-G2 cancer cell death in the presence of spherical colloidal zero-valent gold nanoparticles. Cytotoxicity of zero-valent gold nanoparticles were increased with increasing concentrations (X-axis). Inhibition of cell growth was plotted on the Y-axis.

Figure 7A:
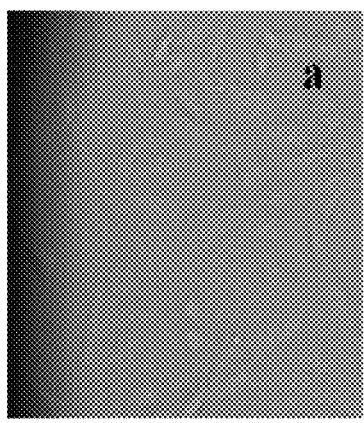
Figure 7B:
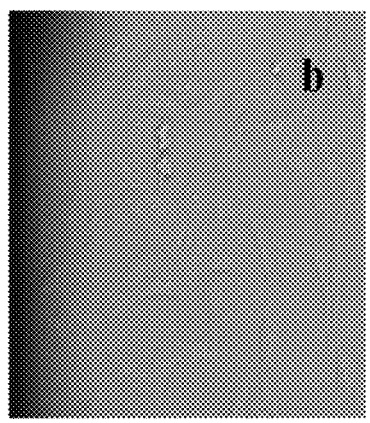
Figure 7C:
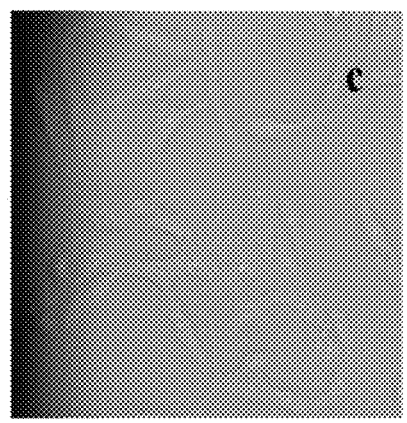
Figure 8A:
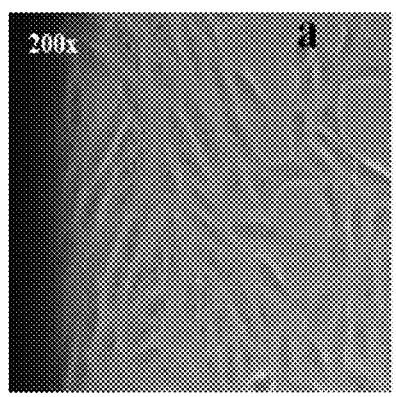
Figure 8B:
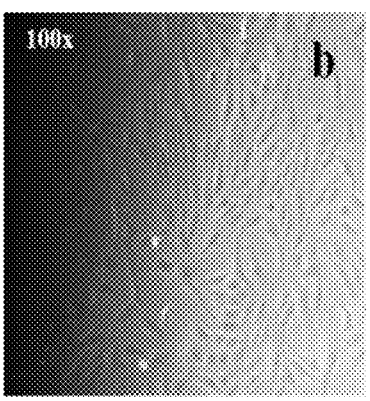
Figure 8C:
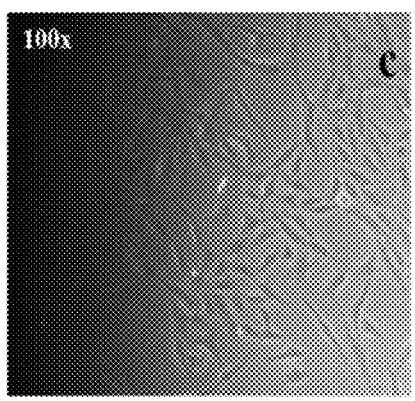
Figure 8D:
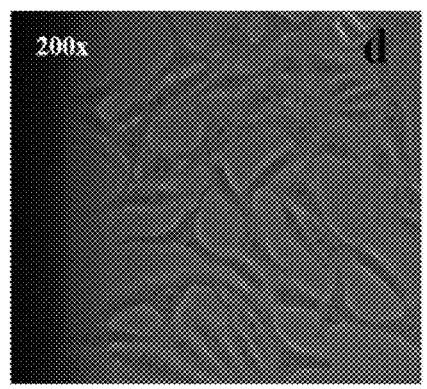
Figure 8E:
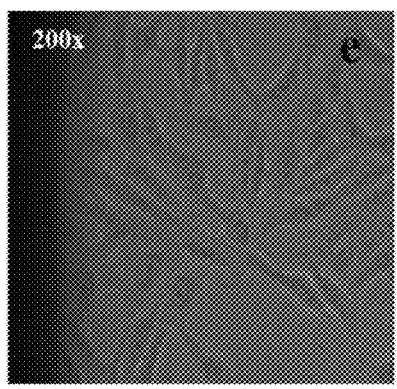

FIGS. 7A-C. Effect of colloidal spherical zero-valent gold nanoparticles on the Hep-G2 cancer cell line after 24 hours of incubation under phase contrast microscope at 200× magnification. (A) Cells without treatment and (b) cell morphological changes were observed at 100.0 µl concentration of zero-valent AuNPs. (C) Cell morphological changes were observed at 125.0 µl zero-valent gold nanoparticles.

FIGS. 8A-E. Morphological changes of Hep-G2 cancer cells treated with zero-valent gold nanoparticles after 36 hr incubation and dose dependent treatment. All the photos were taken under fluorescent microscope: (A) normal Hep-G2 cancer cell without treatment, (B) 100.0 µl dose dependent interaction, (C) image using 100× magnification with 125.0 µl concentration, (D) structural changes observed at 100.0 µl concentration at 200× magnification, and (E) morphological changes at 125.0 µl concentration at 200× magnification.

Figure 9A:
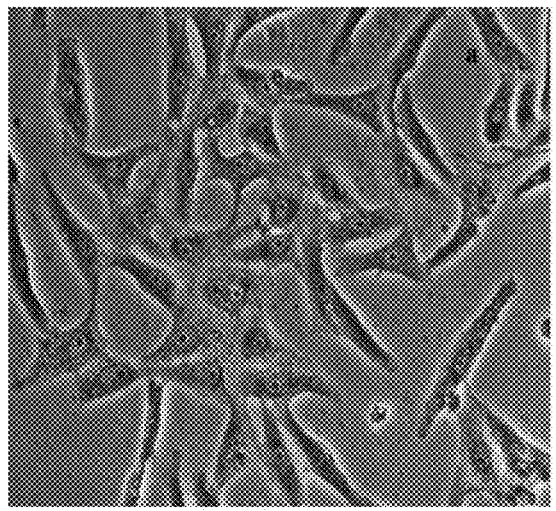
Figure 9B:
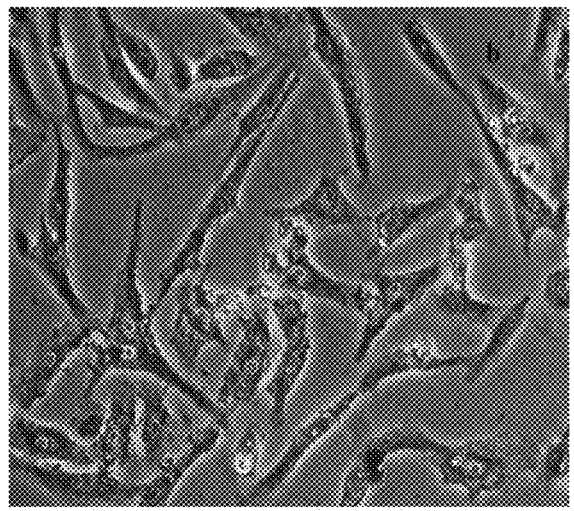
Figure 10A:
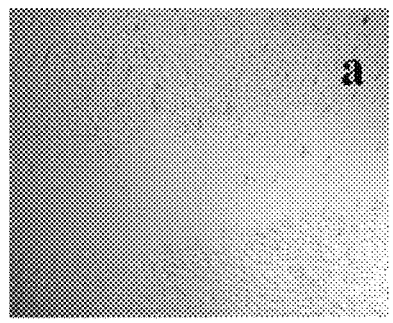
Figure 10B:
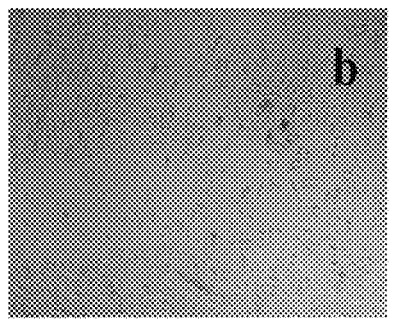
Figure 10C:
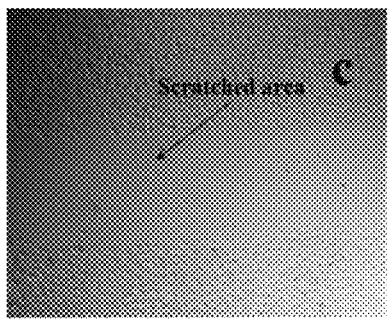
Figure 10D:
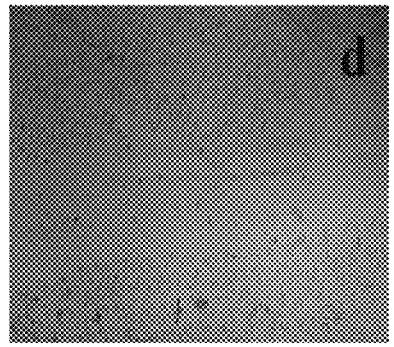
Figure 10E:
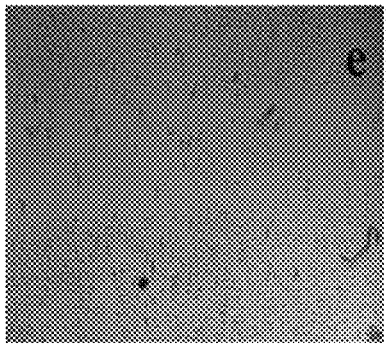
Figure 10F:
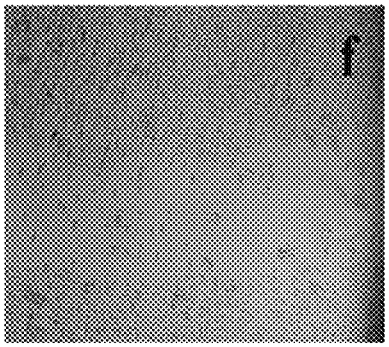
Figure 10G:
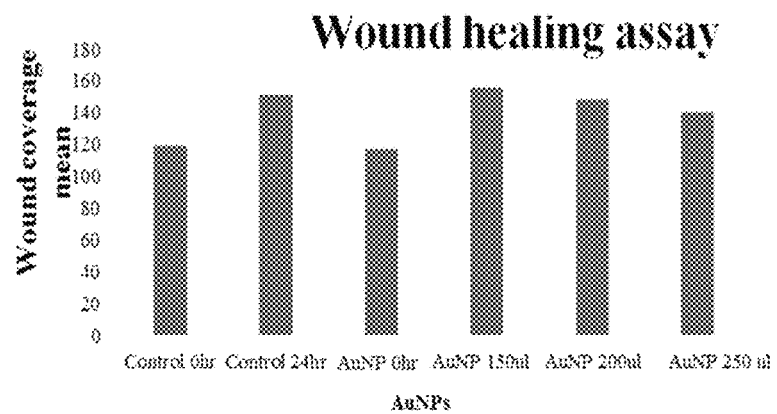

FIGS. 9A-B. The culture of human Hep-G2 cancer cell line with Hoechst staining kit under fluorescent microscope at 200× magnification. (A) Hep-G2 cells without treatment considered as a control. (B) Hep-G2 cells treated with a specific concentration of zero-valent gold nanoparticles for 24 h were stained with Hoechst staining kit (nuclear stained).

FIGS. 10A-G. Zero-valent gold nanoparticles modify the cellular migration of cancer cells in vitro. (A,B) Untreated cells and (C) scratched plate before treatment. When adenocarcinoma cells were treated with (D) 150.0 ul, (E) 200.0 ul, and (F) 250.0 ul spherical zero-valent AuNPs, cell migration width zones were measured by Image J software. (G) Comparative evaluation of treated plates after 24-hour incubation with the control.

DETAILED DESCRIPTION

Embodiments of the disclosure provide zero-valent gold nanoparticles, which are useful for killing cancer cells. Methods described herein may comprise contacting the cancer cells with a solution comprising the zero-valent gold nanoparticles. The nanoparticles may have a size of 10-20 nm, e.g. 12-18 nm, or 14-16 nm. In some embodiments, the zero-valent gold nanoparticles are present in a solution at a concentration of at least 40.0 µM, e.g. at least 50.0 µM, 60.0 µM, 70.0 µM or more.

The zero-valent gold nanoparticles may be prepared by using the standard wet chemical sodium citrate reduction of tetrachloroaurate ($HAuCl_4$) methodology (to resist the aggregation of instantly on nano-formulated zero-valent gold nanoparticles in solution system), for example, the Turkevich method wherein a mild reducing agent trisodium citrate is added to a boiling aqueous solution of $HAuCl_4$. In some embodiments, a 1:2 to 2:1 ratio, e.g. a 1:1 ratio of $HAuCl_4$ to trisodium citrate is used. In some embodiments, the concentration of $HAuCl_4$ and/or trisodium citrate ranges from $2\times10^{-4}$ M to $3\times10^{-4}$ M, e.g. $2.5\times10^{-4}$ M. This method results in the synthesis of monodispersed zero-valent spherical gold nanoparticles. The citrate ion prevents the zero-valent gold nanoparticles from aggregating immediately after formation of zero-valent nanoparticles by providing electrostatic repulsion. In some embodiments, the zero-valent nanoparticles are not coated with any chemical or biological molecule (or drug or active agent).

The zero-valent gold nanoparticles described herein may destroy liver cancer cells either via the apoptosis pathway and/or by forming reactive oxygen species. The cancer cells may be any type of cancer cell including, but not limited to, hepatic, lung, breast, pancreatic, skin, intestinal, brain, kidney, blood, stomach, esophageal, prostate, uterine, cervical, and ovarian cancer cells. In some embodiments, the cancer cells are not contacted with any other anti-cancer active agent. The cells may be contacted with the zero-valent nanoparticles in vitro or may be used in an in vivo method for treating cancer. Thus, in some embodiments, the zero-valent gold nanoparticles are administered to a subject in need thereof to treat a cancer including, but not limited to, hepatic, lung, breast, pancreatic, skin, intestinal, brain, kidney, blood, stomach, esophageal, prostate, uterine, cervical, and ovarian cancer.

A patient or subject to be treated by any of the compositions or methods of the present disclosure can mean either a human or a non-human animal including, but not limited to dogs, horses, cats, rabbits, gerbils, hamsters, rodents, birds, aquatic mammals, cattle, pigs, camelids, and other zoological animals.

In some embodiments, the nano-formulation or active agent is administered to the subject in a therapeutically effective amount. By a "therapeutically effective amount" is meant a sufficient amount to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000.0 mg per adult per day. In particular, the compositions contain 0.01, 0.05, 0.1, 0.5, 1.0, 2.5, 5.0, 10.0, 15.0, 25.0, 50.0, 100.0, 250.0 and 500.0 mg of the active ingredient for the symptomatic adjustment of the dosage to the subject to be treated. A medicament typically contains from about 0.01 mg to about 500.0 mg of the active ingredient, in particular from 1.0 mg to about 100.0 mg of the active ingredient. An effective amount of the drug is ordinarily supplied at a dosage level from 0.0002 mg/kg to about 20.0 mg/kg of body weight per day, especially from about 0.001 mg/kg to 7.0 mg/kg of body weight per day.

Any mode of administration may be used including, but not limited to, transdermal, intraperitoneal, intracranial, intracerebroventricular, intracerebral, intravaginal, intrauterine, oral, rectal, ophthalmic (including intravitreal or intracameral), nasal, topical (including buccal and sublingual), parenteral (including subcutaneous, intraperitoneal, intramuscular, intravenous, intradermal, intracranial, intratracheal, and epidural) administration.

The active agent (zero-valent gold nanoparticles) may be combined with pharmaceutically acceptable excipients. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

All the ratios of reactants or products described herein are mole ratios.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example

Summary

Low-dimensional spherical zero-valent gold nanoparticles ($Au^o$ NPs) were prepared in solution method with citrate-surfactants. Citrate is used here to resist or prevent the aggregation of nano-formulated zero-valent $Au^o$ NPs. The zero-valent $Au^o$ NPs may be used to treat, diagnose, and kill Hep-G2 liver cancer cells due to its electric, structural, and optical properties. Materials that are nano-dimensional in $Au^o$ NPs size can attach to several sites of selected Hep-G2 liver cancer cells and can destroy the cells as well. In this example, we demonstrated quantitative liver cancer cell destruction by using low-dimensional spherical zero-valent $Au^o$ NPs. Low-dimensional zero-valent $Au^o$ NPs are more effective in selectively damaging liver Hep-G2 liver cancer cells compared to other tumor cells and normal cells. To determine the liver cancer cell damage, MTT, trypan blue assay, and morphological changes in hoechst staining solution were observed. Without being bound by theory, it seems that the zero-valent $Au^o$ NPs use an apoptosis mechanism to kill liver Hep-G2 cancer cells by producing cellular dysfunction. The experiments herein point out the importance of zero-valent monodispersed colloidal $Au^o$ NPs to damage Hep-G2 liver cells number in vitro as the viable cell percentage was 98%. As the zero-valent spherical $Au^o$ NPs can bind to specific sites of cancer cells, they represent a new way of destruction of human liver cancer cells.

Materials and Methods

Laboratory grade reagents such as auric chloride, trisodium citrate, and sodium borohydrate chemicals were purchased from the Sigma-Aldrich company (USA) and used as received with further purification. UV/visible spectroscopy was carried out for AuNPs characterization with UV/Vis (300 UV/Visible spectrophotometer, thermo scientific). Dynamic Light Scattering (DLS) measurements were carried out for zero-valent AuNPs characterization using Horiba Particle Size Analyzer LB 550 from Horiba Instruments Inc., Irvine, Calif., USA. Transmission Electron Microscopy (TEM) images for zero-valent AuNPs characterization were acquired on JEOL, JSM-7600F, Japan.

Synthesis of Zero-Valent AuNPs

For the synthesis of surfactant-stabilized zero-valent spherical gold nanoparticles, a modification of an earlier reported technique was used [39,40]. Initially, a 20.0 ml aqueous solution of prepared $2.5 \times 10^{-4}$ M $HAuCl_4$ (Auric chloride) and $2.5 \times 10^{-4}$ M trisodium citrate was made in 250.0 mL Erlenmeyer flask equipped with a magnetic stirring bar and boiled on a hotplate. Next, 0.6 ml of ice-cold 0.1 M freshly prepared sodium borohydride ($NaBH_4$) solution was added into the mixture while stirring. After this addition, the mixture solution immediately turned pink, which indicates the formation of zero-valent spherical AuNPs in aqueous phase. An absorption-band was found at around ~521.0 nm in UV/visible spectrum as well as DLS. TEM images confirmed that the average zero-valent spherical AuNP particle size in this aqueous solution was around 14.8 nm. The synthesized low-dimensional spherical zero-valent AuNPs were totally characterized in detail using the UV-Vis, DLS, and TEM.

Cell Culture and Sub Culture

A liver hepatocellular carcinoma (Hep-G2) cell line obtained from the ATCC was cultured in high glucose medium of DMEM containing 10% fetal bovine serum, 1% penicillin-streptomycin, and 1% glutamine [41]. The cell suspensions were cultured in T25 cm² tissue culture flasks (SPL, Korea #13485) and incubated under standard culture conditions at 37° C. in a 5% $CO_2$ incubator. After reaching 90% confluency, cells were washed twice with phosphate buffered saline (PBS) that contained no calcium and magnesium to remove spent medium and dead cells. The adherent cells were then treated with 0.05% trypsin to detach the entire monolayer of cells. The cell-containing suspension was then transferred to a 15.0 ml centrifuge tube (Greiner, CA #188161) and centrifuged at 1200 rpm for 3 minutes to pellet the cells. The supernatant was discarded and the number of cells was determined by trypan blue assay. The cells were again cultured in a flask and incubated.

Cell Counting

Manual cell counting is still is a popular technique to detect the number of cells as it is cheap and easy to handle. This technique can help to count cell numbers more precisely as it is also capable of showing the dead cells in a sample. For a large number of cells, automated cell counting can be used within a short period of time [42]. A hemocytometer was used to count the cells for these experiments. 20.0 µl of the cells were taken from the cell suspension tube and were mixed with an equal amount of Trypan blue (0.4%) (Gibco, CA #15250-061). Then on the Neubauer chamber, 20.0 µl of the stained cells were loaded for even spread of cells. After settling, live cells were counted in the four corners of the big squares under the fluorescence microscope. The total cell number was determined using the average of four sections. Viable cells were translucent while dead and damaged cells appeared dark blue. The total number of viable cells was calculated using the formula given below:

$$\frac{\text{Total viable cells}}{4} \times 10000 \times \text{Dilution factor} \times \text{Cell count per ml}$$

Freezing of Hep-G2 Cancer Cells

The cell containing medium was washed using PBS, separated by trypsin, and centrifuged for 3 minutes at 1200 RPM to collect the cell pellet. The pellet was re-suspended in a known volume of suspension medium and the cell number was calculated to obtain one million cells for storage. Again, cells were centrifuged and the required volume of preservation medium was added before transfer to appropriately labeled cryovials (Greiner, CA). Before storage in a $N_2$ tank, cells were kept at −80° C. for 24 hr.

Thawing of Frozen Hep-G2 Cancer Cells

Cryovials containing cells were warmed in a water bath and transferred to the biosafety hood. The cells were transfered into a 15.0 ml tube while gradually adding DMEM media containing FBS. The cell suspension was centrifuged and 1 ml of cell suspension media was added to the cell pellet after discarding the supernatant. The cells were cultured in 25.0 cm² tissue culture flasks.

Cell Viability Assay

Trypan blue and MTT assay were performed to measure the number of viable cells. Previously counted (1×10⁶) cells were seeded on coverslips in 24-well plates and grown for 24 hours prior to incubation with gold nanoparticles including 0 µl, 50.0 µl (200.0 uM), 75.0 µl (300.0 uM), 100.0 µl (400.0 uM), and 125.0 µl (500.0 uM). After treatment, cells were put onto the plate, were directly washed using phosphate-buffered saline (PBS, pH7.4) once, trypsinized for 5 min in a 37° C. incubator, and then neutralized with fetal bovine serum (FBS) supplemented growth media. Untreated cells were used as a control. The cells were stained using 4% trypan blue to regulate live cell numbers. The cell count was accomplished manually with a hemocytometer [43].

In MTT assay, 10⁴ cells were plated in 96 well plates (Greiner, CA #655160) and treated with different concentrations of spherical zero-valent AuNPs (0 µM, 40.0 µM, 50.0 µM, 60.0 µM, 70.0 µM, 80.0 µM, 90.0 µM, 100.0 µM). After 24 h of incubation at 37.0° C. in the presence of 5% $CO_2$ atmosphere, cell media was removed. The zero-valent gold nanoparticles were added, and the cells were incubated again for 24 h. 10.0 ul of MTT reagents were added to incubated cells. Purple precipitate was observed after 4 hours of incubation and in each well 100.0 µl of solubilization buffer was added. The plate was incubated again for a certain time at specific conditions at 37.0° C. in the presence of 5% $CO_2$. The absorbance was measured at 570.0 nm by using a microplate ELISA reader with a specific wavelength of 630.0 nm.

Morphological Analysis

Human liver Hep-G2 cancer cells were plated in 6-well plates (5×10⁵ cells per well) and incubated with 100.0 µl and 125.0 µl zero-valent AuNPs for 24 h. Cells cultured in medium without the addition of any nanoparticles were utilized as the control. The cell morphology was thoroughly analyzed and were evaluated using phase contrast microscope (Nikon ECLIPCE TS100, Japan) connected with an imaging system at 24-hour post treatment [44].

Nuclear Staining Assay

To understand deeply the macro-morphological changes in the presence of staining and zero-valent AuNPs, it has been performed a nuclear staining assay. The cover slips were plated in six well plates and 400.0 ul of 0.1% gelatin were thoroughly added and simultaneously incubated for 10 minutes at room temperature. After removal of the coating, the plates containing coverslips were incubated for 15 minutes. Previously counted cells were cultured in the plate containing gelatin-coated coverslips. After 24 hours of incubation, they were washed twice with PBS and 100.0 ul of zero-valent AuNPs were added. 400.0 µL of 2-4% Formaldehyde Fixative Solution were added to each well, and incubated for 20 minutes at room temperature to fix the cells into coverslips. Cells were washed again by PBS and covered with 200.0 ul of Hoechst staining solutions, incubated for 30 minutes at room temperature and analyzed by fluorescence microscopy.

Scratch Wound Healing Assay

In this approach, 1×10⁵ number of Hep-G2 cells were seeded in a 12 well plates and were subjected to 24 hours of incubation at 37.0° C. to form a monolayer of HepG2. A sterile 200.0 ul pipette was used to vertically scratch across each well plate. 1000.0 µl of warmed PBS was used to wash the cell monolayer and gently shake to remove the detached cells. The monolayer was again washed with PBS and DMEM media was added to each well with 150.0 µl, 200.0 ul and 250.0 µl concentrations of spherical zero-valent gold nanoparticles. The untreated plate was considered as a control. All the plates were transferred to the incubator for incubation at 37.0° C. with 5% $CO_2$ for further experimental analysis.

Results

Characterization of Zero-AuNPs by UV/Vis. Spectroscopy

Figure 1:
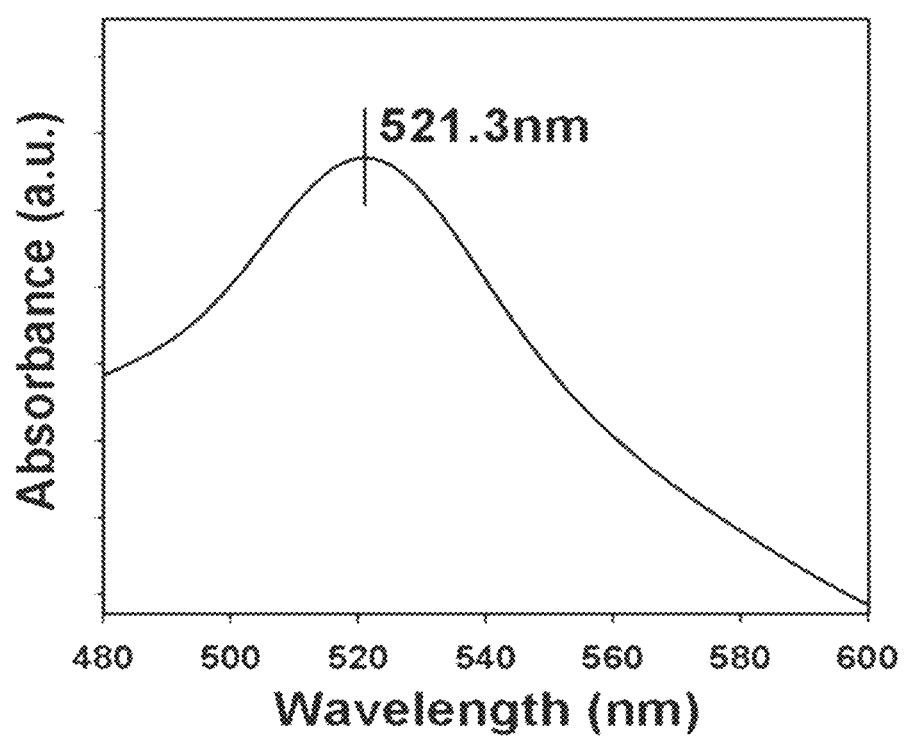
FIG. 1. UV-Vis spectroscopy measurement of the low-dimensional zero-valent gold nanoparticles (Au° NPs).

The characterization was carried out to assess the spectroscopic analyses of the zero-valent gold nanoparticles, which were prepared with Auric chloride, trisodium citrate, and sodium borohydrate. Zero-valent gold nanoparticles exhibits surface plasmon resonance with the oscillation of conductive band electrons in the resonance upon the incident light in a specific wave-length. The surface plasmon resonance of zero-valent AuNPs result in the absorption of light at a wavelength between 500.0 nm and 600.0 nm depending on the size and shape of the produced zero-valent AuNPs. With UV-Vis Spectroscopy, the changes of the zero-valent AuNPs surface for the shifting of plasmon band is measured. The size of the zero-valent gold nanoparticles is increased significantly by the accumulation among nanoparticles as well as binding with ligands, which can cause a red-shift of the Plasmon band. The results of UV/visible spectroscopy of synthesized zero-valent gold nanoparticles is presented in FIG. 1. The UV/visible plasmon bad is found at 521.3 nm.

Characterization of Zero-Valent AuNPs by DLS

Figure 2:
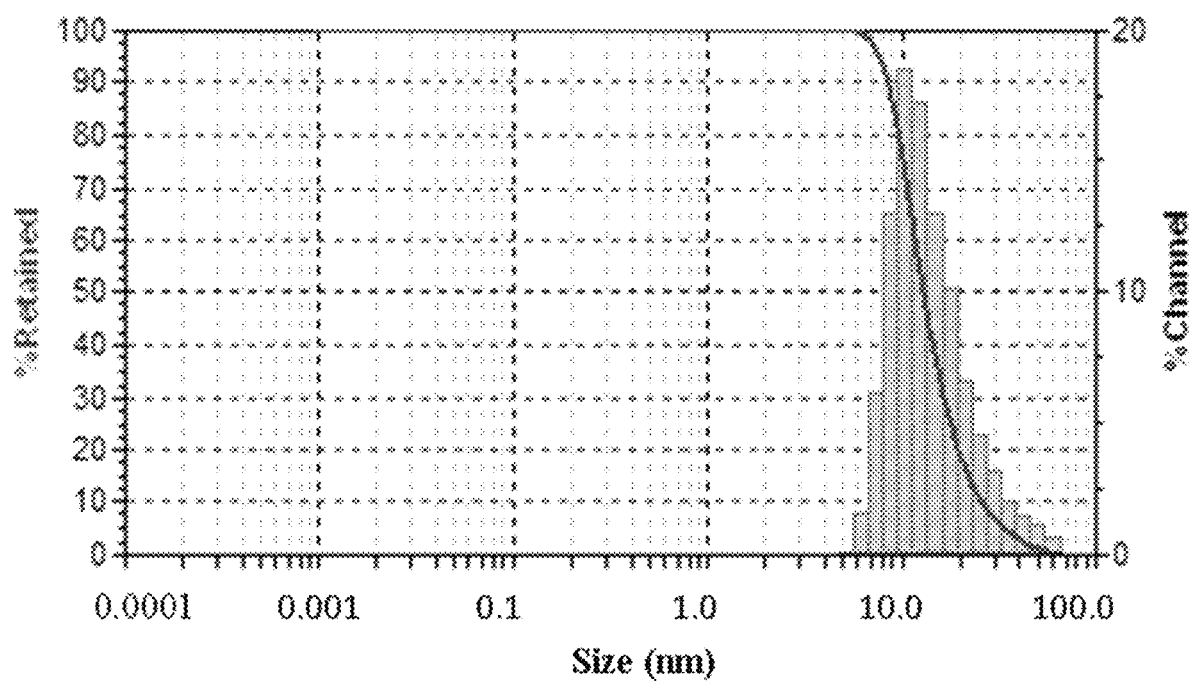
FIG. 2. Dynamic Light Scattering measurement of zero-valent gold nanoparticles (Au° NPs).

Dynamic light scattering (DLS) was used to characterize the synthesized low-dimensional zero-valent gold nanoparticles. This technique is used to analyze the particle size as well as size distribution of prepared zero-valent gold nanoparticles in aqueous medium. The size determined via DLS is usually bigger than TEM. It determines via DLS measurement with the surrounded hydrodynamic layer. That hydrodynamic diameter or layer comprises the prepared particles as well as the electric dipole layer which is attached to the surface of zero-valent gold nanoparticles in the aqueous phase. On the other hand, TEM measures the diameter of the exact image of the particles thus yielding more precise values. The DLS spectra of the sodium citrate functionalized zero-valent gold nanoparticles is displayed and presented in FIG. 2. The average size of the monodispersed as well as stabilized zero-valent gold nanoparticles was found to be 15.7 nm.

Characterization of Zero-Valent AuNPs by TEM

Figures 3A, 3B, 3C:
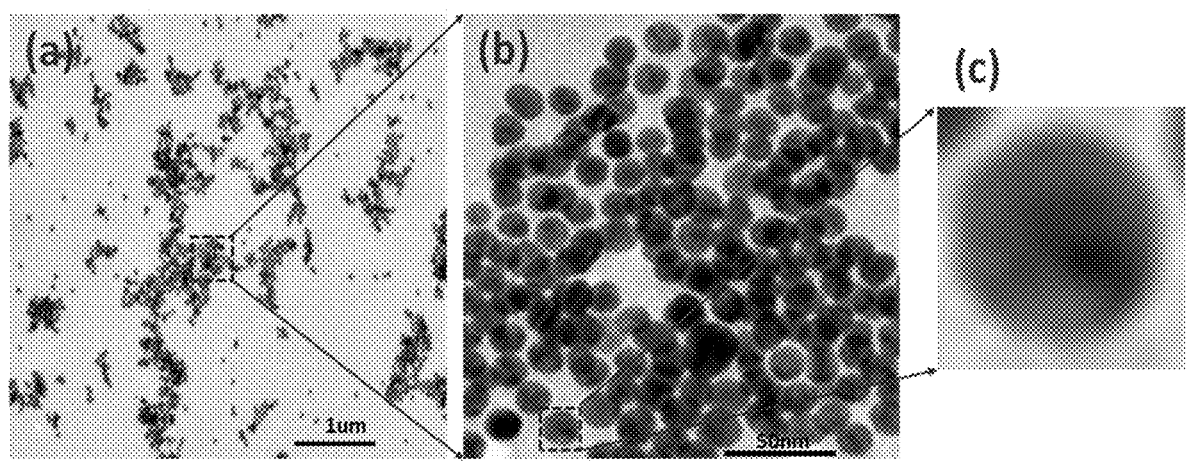
FIGS. 3A-C. TEM images of zero-valent Au° NPs at (A) low, (B) medium (comparatively magnified), and (C) high magnification.
Figure 4A:
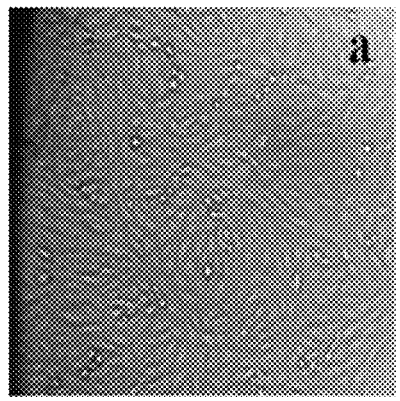
FIGS. 4A-E. Zero-valent gold nanoparticles (Au° NPs) dependent human liver cancer cell (Hep-G2) destruction. Cell damage was observed under a fluorescence microscope at 100× magnification. (A) No gold nanoparticles was considered as a control. (B) Cell death using 50.0 µl of zero-valent gold nanoparticle (Au° NPs), (C) 75.0 µl of zero-valent gold nanoparticles (Au° NPs), (D) 100.0 µl of zero-valent gold nanoparticles (Au° NPs), and (E) 125.0 µl of zero-valent gold nanoparticles (Au° NPs).
Figure 4B:
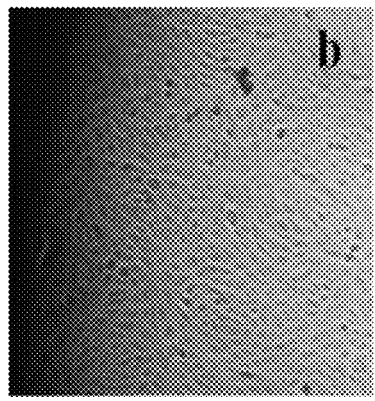
Figure 4C:
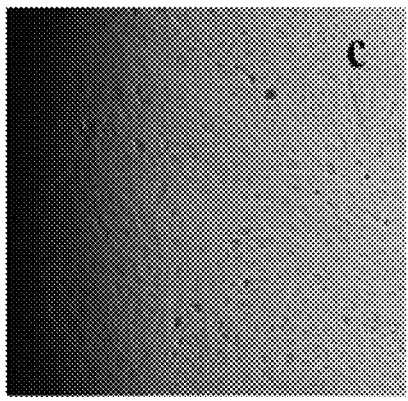
Figure 4D:
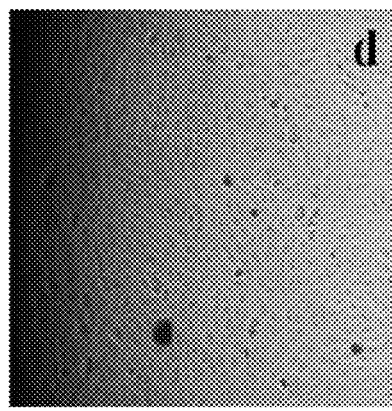
Figure 4E:
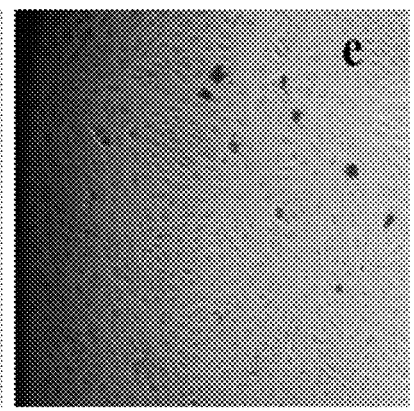

The morphology of the stabilized monodispersed zero-valent gold nanoparticle was analyzed using Transmission electron microscopy (TEM). The zero-valent gold nanoparticles show the particles to be uniformly dispersed with negligible aggregation in the aqueous system due to the presence of sodium citrate. The TEM image of the functionalized zero-valent gold nanoparticle is displayed in FIG. 3. The uniformity of the size and shape of the dispersed zero-valent gold nanoparticle is clearly demonstrated in FIG. 3a-c (low-magnified, medium-magnified, and highly-magnified images). The average size of the functionalized AuNPs is 14.8 nm as displayed in FIG. 3b,c (high-magnified image).

Anticancer Activity of Zero-Valent AuNPs

Figure 5A:
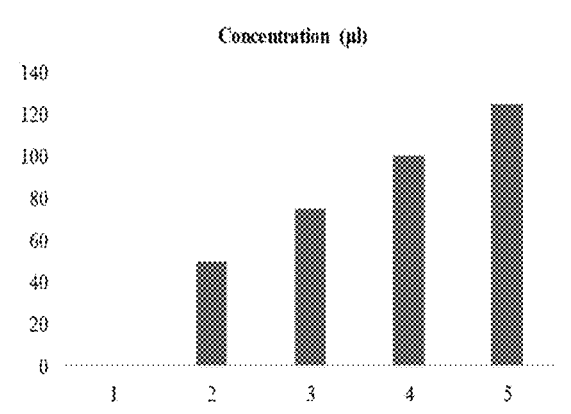
FIGS. 5A-B. Cell death induced by zero-valent gold nanoparticles (Au° NPs). Hep-G2 liver cancer cells were incubated with five different concentrations of zero-valent gold nanoparticles and destruction was followed. The cell death was calculated using a hematocytometer. (A) Several concentrations (0 µl, 50.0 µl, g, 75.0 µl, 100.0 µl and 125.0 µl) of zero-valent gold nanoparticles used in this experiment.
Figure 5B:
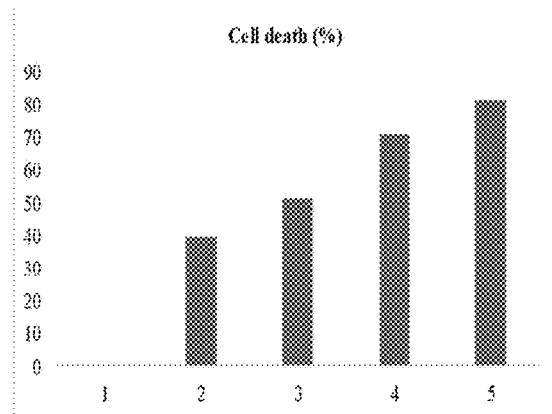

Generally, nanoparticles usually have a smaller size (2-10 nm) with a larger surface area and release higher energy when going to the resting state [45,46]. Due to the small size, they are capable of entering the target cell such as a cancer cell or microbes to prevent metastasis or growth by blocking the self-renewal capability of these cells [47]. One million cells were plated in 12 well plates. After 24 hour incubation, cells were analyzed by fluorescence microscope, then the cells were treated with 0 µl, 50.0 µl, g, 75.0 µl, 100.0 µl and 125.0 µl concentrations of zero-valent gold nanoparticles. The antitumor activity was analyzed after 24 hr of cell treatment (FIG. 4). The cells were washed with PBS, centrifuged and the cell number was calculated (FIG. 5). The following formula (i) was used to count percentage of cell death:

$$\text{Total death cell}=(\text{Total cell}-\text{live cell})/\text{Total cell}\times 100\% \qquad (i)$$

Anticancer activity was evaluated by MTT assay and it was found that the cytotoxicity of spherical zero-valent $Au^\circ$ NPs were increased with increasing concentrations (FIG. 6). There was no cell death observed in control (0 µl $Au^\circ$ NPs), but with 40.0 µM, 50.0 µM, 60.0 µM, 70.0 µM, 80.0 µM, 90.0 µM, 100.0 µM concentrations cell death was gradually increased. Concentration and molarity is an important determinant to achieve complete mortality. Complete destruction of Hep-G2 cancer cells can be achieved in a dose dependent manner Identification of Cell Morphological Changes Low-dimensional spherical dispersed zero-valent gold nanoparticles can change the internal and external structure of the cells. Cells were cultured ($1\times10^6$) in 12 well plates, incubated and analyzed via florescence microscope (FIG. 7). After treatment of cell with the zero-valent gold nanoparticles, cells damage and changes in cell shape were analyzed (FIG. 8) by using the same microscope at 24 hour and 36 hours respectively.

The effect of spherical zero-valent $Au^\circ$ nanoparticles on the cancer cell line was assessed. The treated cells appeared blue as the stain directly reached the nuclei and was able to bind to the condensed chromatin and DNA grooves. Hep-G2 cells appeared blue and the zero-valent gold nanoparticles also bound to the membrane of cancer cells, rupture the membrane, and cause cell death (FIG. 9).

DISCUSSION

Mechanism of Hep-G2 Cancer Cell Destruction

Generally, nanoparticles are widely using in cancer treatment and diagnosis due to its lower toxic effect, inert properties, and greater tissue distribution which allows for more rapid penetration of cells [48]. Nanoparticles can adsorb protein from the biological system under specific conditions and produce reactive oxygen species (ROS) and induce apoptosis [49]. The maximum effect of nanoparticles damaging the cell depends on the particle size. Particles having a size of 9.0 nm or less have the ability to cross the nuclear pore complex by diffusion while particles up to 39.0 nm can easily penetrate the membrane and enter the cell nucleus [50]. It has been assumed that nanoparticles hinder proper function of mitochondria and produce the cell death either by entering mitochondria easily or binding with liposomes and fusing in the mitochondrial membrane or by destroying lipid bilayers and enhancing cell death [51-53]. From our experiments, it is shown that zero-valent spherical AuNPs bind to the receptor of the cell surface. Then, the zero-valent AuNPs either bind with lysosome or enter into the mitochondria via a diffusion process. After entering the cell, the particles can also penetrate the nucleus and cause irreversible destruction of the cancer cell.

Control Experiment

An in vitro wound healing assay may be used to see the cell migration associated with metastasis of cancer cells in the body after using several medications [54]. Briefly, the cells were seeded, scratched, treated, incubated and images were taken by phase contrast microscope. In our experiment, previous data showed that zero-valent AuNPs were able to kill the cells significantly and effectively. We used slightly more cells compared to the usual protocol to see the effect at several concentrations. The width mean was measured using the Image J software. There is no significant difference between the control 0-hour and spherical zero-valent AuNPs 0-hour migration. After 24 of incubation, the migration rate is decreased gradually (FIG. 10a-g) by using zero-valent $Au^o$ NPs (150.0 ul, 200.0 ul, 250.0 ul). Additionally, blank (control 24 hr) is showed a higher level of migration.

CONCLUSION

In this Example, low-dimensional nano-formulated zero-valent spherical gold nanoparticles were prepared by active reducing agent (sodium borohydrate in presence of sodium citrate) in aqueous phase. The prepared zero-valent $Au^o$ NPs particles were totally characterized by using UV-Vis spectrometry as well as DLS studies. The morphology of the zero-valent gold nanoparticles was also examined using TEM. These monodispersed zero-valent $Au^o$ NPs efficiently destroyed Hep-G2 cancer cells by following the apoptosis pathway and forming reactive oxygen species (ROS). A significant number of cell death occurred with an increasing concentration of the zero-valent $Au^o$ NPs. Therefore, the low-dimensional $Au^o$ NPs described herein are a useful anti-cancer treatment.

Acknowledgements

This project was funded by the National Plan for Science, Technology and Innovation (MAARIFAH)—King Abdulaziz City for Science and Technology—the Kingdom of Saudi Arabia—award number (14-BIO1978-03). The inventors also acknowledge with thanks Science and Technology Unit, King Abdulaziz University for technical support.

REFERENCES

1. Elahi, N., Kamali, M., & Baghersad M. H., Recent biomedical applications of gold nanoparticles: A review, Talanta, 2018, 184, 537-556.
2. W. Ghann, T. Harris, D. Kabir, H. Kang, M. Jim, M. M. Rahman, M. M. Ali, J. Uddin. Lipoic acid decorated gold nanoparticles and their application in the detection of Lead ions. Journal of Nanomedicine & Nanotechnology 2019, 10, 539.
3. Huang, X. & El-Sayed, M. A., Gold nanoparticles: Optical properties and implementations in cancer diagnosis and photothermal therapy, Journal of Advanced Research. 2001, 1, 13-28.
4. Dykman, L., and Khlebtsov, N. Gold nanoparticles in biomedical applications: recent advances and perspectives. Chem. Soc. Rev. 2012, 41, 2256-2282.
5. Athukorale, S., et al. NaHS induces complete nondestructive ligand displacement from aggregated gold nanoparticles. J. Phys. Chem. C, 2018, 122, 2137-2144.
6. Zhou, X., Xu, W., Liu, G., Panda, D., & Chen, P. Size-dependent catalytic activity and dynamics of gold nanoparticles at the single-molecule level. J. Am. Chem. Soc., 2010 132, 138-146.
7. Dreaden E. C., Austin L. A., Mackey M. A., El-Sayed M. A., Size matters: gold nanoparticles in targeted cancer drug delivery. TherDeliv. 2012, 3, 457-478.
8. Cole L E, Ross R D, Tilley J M R, Vargo-Gogola T, Roeder R K. Gold nanoparticles as contrast agents in x-ray imaging and computed tomography. Nanomedicine, 2015; 10, 321-341.
9. Saha, K. Agasti, S. S., Kim, C., Li, X. & Rotello, V. M., Gold Nanoparticles in Chemical and Biological Sensing. Chemical Reviews, 2012, 112, 2739-2779.
10. Wang, D., et al. Recent Advances in SPR Imaging Sensors. Sensors, 2019, 19, 12-66.
11. El-Sayed, M. A. Some Interesting Properties of Metals Confined in Time and Nanometer Space of Different Shapes Acc. Chem. Res. 2001, 34, 257-264.
12. Zheng, T., Bott, S., & Huo, Q. Techniques for Accurate Sizing of Gold Nanoparticles Using Dynamic Light Scattering with Particular Application to Chemical and Biological Sensing Based on Aggregate Formation. ACS Appl. Materials & Interfaces. 2016, 8, 21585-21594.
13. Liu, J.; Cao, Z.; Lu, Y. Functional nucleic acid sensors. Chem. Rev. 2009, 109, 1948-1998.
14. Slocik, J. M., Zabinski, J. S., Phillips, D. M., Naik, R. R. Colorimetric response of peptide-functionalized gold nanoparticles to metal ions. Small, 2008, 4, 548-551.
15. Si, S., Raula, M., Paira, T. K., Mandal, T. K. Reversible self-assembly of carboxylated peptide-functionalized gold nanoparticles driven by metal-ion coordination. Chem. Phys. Chem. 2008, 9, 1578-1584.
16. Hutter E., Pileni M-P. J. Detection of DNA Hybridization by Gold Nanoparticle Enhanced Transmission SPR Spectroscopy. Phys. Chem. B. 2003, 107, 6497-6499.
17. Lee, J. S., Han, M. S., Mirkin, C. A. Angew. Colorimetric detection of mercuric ion ($Hg^{2+}$) in aqueous media using DNA-functionalized gold nanoparticles. Chem., Int. Ed. 2007, 46, 4093-4096.
18. Liu, C. W., Huang, C. C., Chang, H. T. Control over surface DNA density on gold nanoparticles allows selective and sensitive detection of mercury (II). Langmuir. 2008, 24, 8346-8350.
19. Chai, F., Wang, C. G., Wang, T. T., Ma, Z. F., Su, Z. M. Fluorescent Gold Nanoprobes for the Sensitive and Selective Detection for Hg. Nanotechnology. 2010, 21, 025501.
20. Perez-Herrero, E. & Fernandez-Medarde, A. Advanced targeted therapies in cancer: Drug nanocarriers, the future of chemotherapy. Eur. J. Pharm. & Biopharm. 2015; 93, 52-79.
21. Naz, S. et al. Advances in therapeutic implications of inorganic drug delivery nano-platforms for cancer. Int. J. Mol. Sci. 2019; 20, 965.
22. Vallet-Regi, M. & Tamanoi, F. Overview of studies regarding mesoporous silica nanomaterials and their biomedical application. Enzymes. 2018; 43, 1-10.
23. Yanes, R. E. & Tamanoi, F. Development of mesoporous silica nanomaterials as a vehicle for anticancer drug delivery. Therapeutic Delivery. 2012, 3, 389-404.
24. Mekaru, H., Lu, J. & Tamanoi, F. Development of mesoporous silica-based nanoparticles with controlled release capability for cancer therapy. Adv. Drug. Deliv. Rev. 2015, 95, 40-49.
25. Daniel, M. C., Astruc, D. Gold Nanoparticles: Assembly, Supramolecular Chemistry, Quantum-Size-Related Properties, and Applications toward Biology, Catalysis, and Nanotechnology. Chemical Reviews. 2004:104; 293-346.
26. Dash, S. S., Bag, B. G. Synthesis of gold nanoparticles using renewable Punica granatum juice and study of its catalytic activity. Applied Nanoscience. 2012: 4; 55-59.
27. Jemal A, Bray F, Center M M, Ferlay J, Ward E, Forman D, et al. Global cancer statistics. CA Cancer J Clin. 2011; 61: 69-90.
28. Nikoletopoulou V, Markaki M, Palikaras K, Tavernarakis N. Crosstalk between apoptosis, necrosis and autophagy. Biochem Biophys Acta. 2013; 1833: 3448-3459.

29. Rello-Varona S, Herrero-Martín D, López-Alemany R, Muñoz-Pinedo C, Tirado O M. Not) all (dead) things share the same breath: identification of cell death mechanisms in anticancer therapy. Can Res. 2015; 75: 913-917.
30. Kashyap, M., Tiwari, A., Arya, K., Saxena, V. L. Quantum Dot: An Emerging Nano-crystal for cancer diagnosis and Therapy. Research Journal of Life Sciences, Bioinformatics, Pharmaceutical and Chemical Sciences. 2019; 5, 320.
31. Rao P V, Nallappan D, Madhavi K, Rahman S, Jun Wei L, Gan S H. Phytochemicals and biogenic metallic nanoparticles as anticancer agents. Oxidative Med Cell Longev. 2016; 2016: 3685671.
32. Shim G, Kim M G, Kim D, Park J Y, Oh Y K. Nanoformulation-based sequential combination cancer therapy. Advanced drug delivery reviews. 2017; 115: 57-81.
33. Liong, M. et al. Multifunctional inorganic nanoparticles for imaging, targeting and drug delivery. ACS Nano 2006, 2, 889-896.
34. Lu, J., Liong, M., Li, Z., Zink, J. I. & Tamanoi, F. Biocompatibility, biodistribution, and drug delivery efficiency of mesoporous silica nanoparticles for cancer therapy in animals. Small. 2010, 6, 1794-1805.
35. Tomić S, Đokić J, Vasilijić S, et al. Size-dependent effects of gold nanoparticles uptake on maturation and antitumor functions of human dendritic cells in vitro. PLoS One. 2014; 9: e96584.
36. Condeelis J, Pollard J W. Macrophages: obligate partners for tumor cell migration, invasion, and metastasis. Cell. 2006; 124: 263-266.
37. Yuan, Y., Zhang, S., Hwang, J., Kong, I. Silver Nanoparticles Potentiates Cytotoxicity and Apoptotic Potential of Camptothecin in Human Cervical Cancer Cells. Oxidative Medicine and Cellular Longevity. 2018; 2018: 1-21.
38. Hardman R A toxicologic review of quantum dots: toxicity depends on physicochemical and environmental factors. Environ Health Perspect.2006; 114, 165-172.
39. Ghann, W., Harris, T., Kabir, D., Kang, H., Jim, M., Rahman, M. M., Ali, M. A., Uddin, J. Lipoic Acid Decorated Gold Nanoparticles and their Application in the Detection of Lead Ions. Journal of Nanomedicine & Nanotechnology 2019, 10, 539.
40. Shiddiky, M. J. A., Shim, Y. B. Trace analysis of DNA: Preconcentration, separation, and electrochemical detection in microchip electrophoresis using Au nanoparticles. Anal. Chem. 2017, 79, 3724-3733.
41. Choi Y. J., Park J. H., Han J. W., Kim, E., Jae-Wook, O., Lee, S. Y., Kim, J. H., Gurunathan S. Differential Cytotoxic Potential of Silver Nanoparticles in Human Ovarian Cancer Cells and Ovarian Cancer Stem Cells. Int J Mol Sci. 2016, 17, 2077.
42. Cadena-Herrera D, Lara J E D, Ramírez-Ibañez ND, López-Morales C A, Pérez N O, Flores-Ortiz L F, Medina-Rivero E. Validation of three viable-cell counting methods: Manual, semi-automated, and automated. Biotechnology Reports. 2015, 7; 9-16.
43. Yuan Y G, Zhang S, Hwang J Y, Kong I K. Silver Nanoparticles Potentiates Cytotoxicity and Apoptotic Potential of Camptothecin in Human Cervical Cancer Cells. Oxid Med Cell Longev. 2018, 12; 6121328.
44. Yuan, Y., Zhang, S., Hwang, J., Kong, I. Silver Nanoparticles Potentiates Cytotoxicity and Apoptotic Potential of Camptothecin in Human Cervical Cancer Cells. Oxidative Medicine and Cellular Longevity. 2018; 2018: 1-21.
45. Goharshadi E K, Sajjadi S H, Mehrkhah R, Nancarrow P. Sonochemical synthesis and measurement of optical properties of zinc sulfide quantum dots. Chem Eng J. 2012; 209: 113-117.
46. Kimling J, Maier M, Okenve B, Kotaidis V, Ballot H, Plech A. Turkevich method for gold nanoparticle synthesis revisited. J Phys Chem B. 2006; 110: 15700-15707.
47. Wahab R, Kaushik N, Khan F, Kaushik N K, Lee S J, Choi E H, Al-Khedhairy A A. Gold quantum dots impair the tumorigenic potential of glioma stem-like cells via β-catenin downregulation in vitro. International Journal of Nanomedicine, 2019; 14: 1131-1148.
48. Johnston, H., Hutchison, G., Christensen, F., Peters, S., Hankin, S., Stone, V. A review of the in vivo and in vitro toxicity of silver and gold particulates: particle attributes and biological mechanisms responsible for the observed toxicity. Crit Rev Toxicol 2010; 40: 328-46.
49. Xu, R., Ma, J., Sun, X., Chen, Z., Jiang, X., Guo, Z., Huang, L., Li, Y., Wang, M., Wang, C., Liu, J., Fan, X., Gu, J., Chen, X., Zhang, Y., Ning, G. Ag nanoparticles sensitize IR-induced killing of cancer cells. Cell Research.2009; 19: 1031-1034.
50. Panté, N., Kann, M. Nuclear pore complex is able to transport macromolecules with diameters of –39 nm. Mol Biol Cell. 2002; 13: 425-34.
51. Salnikov, V., Lukyanenko, Y. O., Frederick, C. A., Lederer, W. J., Lukyanenko, V. Probing the outer mitochondrial membrane in cardiac mitochondria with nanoparticles. Biophys J. 2007; 92: 1058-71.
52. Yamada, Y., Akita, H., Kamiya, H., Kogure, K., Yamamoto, T., Shinohara, Y. Mito-porter: A liposome-based carrier system for delivery of macromolecules into mitochondria via membrane fusion. Biochim. Biophys. Acta. 2008; 1778: 423-32.
53. Wang, L., Jiang, X., Ji, Y., Bai, R., Zhao, Y., Wu, X. Surface chemistry of gold nanorods: Origin of cell membrane damage and cytotoxicity. Nanoscale. 2013; 5: 8384-91.
54. Kovács, D., Igaz, N., Marton, A., Rónavári, A., Bélteky, P., Bodai, L., Spengler, G., Tiszlavicz, L., Razga, Z., Hegyi, P., Vizier, C., Boros, I. M., Kónya, Z., Kiricsi, M. Core-shell nanoparticles suppress metastasis and modify the tumour-supportive activity of cancer-associated fibroblasts. Journal of Nanobiotechnology 2020; 18: 18.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of killing liver cancer cells, comprising contacting the liver cancer cells with a solution comprising monodispersed zero-valent spherical gold nanoparticles ($Au^o$ NPs), wherein the $Au^o$ NPs have a diameter of 10-20 nm and wherein the $Au^o$ NPs are uncoated, wherein the liver cancer cells are Hep-G2 liver cancer cells.

2. The method of claim 1, wherein the $Au^o$ NPs are present in the solution at a concentration of at least 40.0 µM.

3. The method of claim 1, wherein the liver cancer cells are not contacted with any other anti-cancer agent.

4. The method of claim 1, wherein the $Au^o$ NPs induce production of reactive oxygen species (ROS) and/or induce apoptosis of the liver cancer cells.

5. A method of treating liver cancer in a subject in need thereof, comprising administering to the subject a therapeutically effective amount of a composition comprising Au° NPs, wherein the Au° NPs have a diameter of 10-20 nm and wherein the Au° NPs are uncoated, wherein the Au° NPs are administered in an amount sufficient to induce production of reactive oxygen species (ROS) and/or induce apoptosis of Hep-G2 liver cancer cells.

6. The method of claim 5, wherein the Au° NPs are present in the composition at a concentration of at least 40.0 µM.

7. The method of claim 5, wherein the Au° NPs are administered without any other anti-cancer agent.

* * * * *